(12) United States Patent
Buchberger et al.

(10) Patent No.: US 10,765,147 B2
(45) Date of Patent: Sep. 8, 2020

(54) AEROSOL FORMING COMPONENT

(71) Applicant: BATMARK LIMITED, London (GB)

(72) Inventors: Helmut Buchberger, St. Florian (AT); Colin John Dickens, London (GB); Rory Fraser, London (GB)

(73) Assignee: BATMARK LIMITED, London (GB)

( * ) Notice: Subject to any disclaimer, the term of this patent is extended or adjusted under 35 U.S.C. 154(b) by 325 days.

(21) Appl. No.: 15/307,095

(22) PCT Filed: Apr. 27, 2015

(86) PCT No.: PCT/GB2015/051213
§ 371 (c)(1),
(2) Date: Oct. 27, 2016

(87) PCT Pub. No.: WO2015/166219
PCT Pub. Date: Nov. 5, 2015

(65) Prior Publication Data
US 2017/0042245 A1    Feb. 16, 2017

(30) Foreign Application Priority Data

Apr. 28, 2014 (GB) .................................. 1407426.4

(51) Int. Cl.
*A24F 47/00* (2020.01)
*A61M 15/06* (2006.01)
(Continued)

(52) U.S. Cl.
CPC ......... *A24F 47/008* (2013.01); *A61M 11/042* (2014.02); *A61M 15/0021* (2014.02);
(Continued)

(58) Field of Classification Search
CPC ............... A24F 47/008; A61M 11/042; A61M 15/0021; A61M 15/06; A61M 15/0086;
(Continued)

(56) References Cited

U.S. PATENT DOCUMENTS 2,057,353 A   10/1936 Whittemore
2,809,634 A   10/1957 Murai
(Continued)

FOREIGN PATENT DOCUMENTS

AT   508244   12/2010
AT   510405   4/2012
(Continued)

OTHER PUBLICATIONS

International Search Report and Written Opinion dated Feb. 6, 2013 for PCT/EP0212/070647 filed Oct. 18, 2012.
(Continued)

*Primary Examiner* — Jimmy Chou
(74) *Attorney, Agent, or Firm* — Patterson Thuente Pedersen, P.A.

(57) ABSTRACT

An aerosol forming component for volatilizing a liquid in an aerosol delivery device is disclosed. The aerosol forming component includes a first aerosol-forming member configured to be heated up to a first operating temperature and thereafter to a second higher operating temperature, and a second aerosol-forming member configured to be heated up to at least the first operating temperature as the first aerosol-forming member reaches the second higher operating temperature so that liquid volatilized from the two aerosol-forming members mix with one another.

8 Claims, 4 Drawing Sheets

(51) Int. Cl.
*A61M 11/04* (2006.01)
*B05B 7/16* (2006.01)
*A61M 15/00* (2006.01)
*H05B 3/12* (2006.01)
*A61M 16/00* (2006.01)

(52) U.S. Cl.
CPC ........... *A61M 15/06* (2013.01); *B05B 7/1686* (2013.01); *H05B 3/12* (2013.01); *A61M 15/0086* (2013.01); *A61M 2016/0021* (2013.01); *A61M 2016/0027* (2013.01); *A61M 2016/0039* (2013.01); *A61M 2202/0468* (2013.01); *A61M 2205/3368* (2013.01); *A61M 2205/3653* (2013.01); *A61M 2205/50* (2013.01); *A61M 2205/8206* (2013.01); *H05B 2203/021* (2013.01)

(58) Field of Classification Search
CPC .. A61M 2016/0021; A61M 2016/0027; A61M 2016/0039; A61M 2202/0468; A61M 2205/3368; A61M 2205/50; A61M 2205/8206; A61M 2205/3653; B05B 7/1686; H05B 3/12; H05B 2203/021
USPC ................ 219/494, 525, 201; 131/328, 329; 128/203.27
See application file for complete search history.

(56) References Cited

U.S. PATENT DOCUMENTS

| | | | |
|---|---|---|---|
| 3,111,396 A | 11/1963 | Ball | |
| 3,402,724 A * | 9/1968 | Blount | A24F 13/04 131/198.1 |
| 3,431,393 A | 3/1969 | Katsuda | |
| 3,433,632 A | 3/1969 | Elbert | |
| 3,521,643 A | 7/1970 | Toth | |
| 3,604,428 A | 9/1971 | Moukaddem | |
| 3,804,100 A | 4/1974 | Fariello | |
| 3,964,902 A | 6/1976 | Fletcher | |
| 4,009,713 A | 3/1977 | Simmons | |
| 4,031,906 A | 6/1977 | Knapp | |
| 4,094,119 A | 6/1978 | Sullivan | |
| 4,145,001 A | 3/1979 | Weyenberg | |
| 4,161,283 A | 7/1979 | Hyman | |
| 4,193,513 A | 3/1980 | Bull | |
| 4,503,851 A | 3/1985 | Brauroth | |
| 4,588,976 A | 5/1986 | Jaselli | |
| 4,676,237 A | 6/1987 | Wood | |
| 4,677,992 A | 7/1987 | Bliznak | |
| 4,735,217 A | 4/1988 | Gerth | |
| 4,830,028 A | 5/1989 | Lawson | |
| 4,848,374 A | 7/1989 | Chard | |
| 4,885,129 A | 12/1989 | Leonard | |
| 4,917,301 A | 4/1990 | Munteanu | |
| 4,922,901 A * | 5/1990 | Brooks | A24F 47/006 128/202.27 |
| 4,947,874 A | 8/1990 | Brooks | |
| 4,947,875 A | 8/1990 | Brooks | |
| 4,978,814 A | 12/1990 | Honour | |
| 5,027,837 A | 7/1991 | Clearman | |
| 5,046,514 A | 9/1991 | Bolt | |
| 5,060,671 A * | 10/1991 | Counts | A24F 47/008 131/329 |
| 5,095,647 A | 3/1992 | Zobele | |
| 5,095,921 A * | 3/1992 | Losee | A24F 47/008 131/194 |
| 5,096,921 A | 3/1992 | Bollinger | |
| 5,099,861 A | 3/1992 | Clearman et al. | |
| 5,121,881 A | 6/1992 | Lembeck | |
| 5,167,242 A | 12/1992 | Turner | |
| 5,179,966 A * | 1/1993 | Losee | A24F 47/008 128/202.21 |
| 5,247,947 A | 9/1993 | Clearman | |
| 5,269,327 A * | 12/1993 | Counts | A24F 47/008 128/200.14 |
| 5,322,075 A | 6/1994 | Deevi | |
| 5,388,574 A | 2/1995 | Ingebrethsen | |
| 5,390,864 A | 2/1995 | Alexander | |
| 5,408,574 A * | 4/1995 | Deevi | A24F 47/008 128/202.21 |
| 5,479,948 A | 1/1996 | Counts | |
| 5,497,792 A | 3/1996 | Prasad | |
| 5,501,236 A | 3/1996 | Hill | |
| 5,505,214 A * | 4/1996 | Collins | H05B 3/24 131/194 |
| 5,530,225 A * | 6/1996 | Hajaligol | A24F 47/008 131/194 |
| 5,540,241 A | 7/1996 | Kim | |
| 5,553,791 A | 9/1996 | Alexander | |
| 5,636,787 A | 6/1997 | Gowhari | |
| 5,649,554 A * | 7/1997 | Sprinkel | A24F 47/008 128/202.21 |
| 5,659,656 A * | 8/1997 | Das | A24F 47/008 219/121.63 |
| 5,666,977 A * | 9/1997 | Higgins | A24F 47/008 128/200.14 |
| 5,692,291 A | 12/1997 | Seetharama | |
| 5,743,251 A | 4/1998 | Howell et al. | |
| 5,865,185 A | 2/1999 | Collins | |
| 5,878,752 A * | 3/1999 | Adams | A24F 47/008 131/329 |
| 6,040,560 A | 3/2000 | Fleischhauer | |
| 6,058,711 A | 5/2000 | Maciaszek | |
| 6,095,505 A | 8/2000 | Miller | |
| 6,155,268 A | 12/2000 | Takeuchi | |
| 6,275,650 B1 | 8/2001 | Lambert | |
| 6,652,804 B1 | 11/2003 | Neuann | |
| 6,681,998 B2 | 1/2004 | Sharpe | |
| 6,701,921 B2 | 3/2004 | Sprinkel | |
| 6,790,496 B1 | 9/2004 | Levander | |
| 7,100,618 B2 | 9/2006 | Dominquez | |
| 7,112,712 B1 | 9/2006 | Ancell | |
| 7,263,282 B2 | 8/2007 | Meyer | |
| 7,400,940 B2 | 7/2008 | McRae | |
| 7,540,286 B2 | 6/2009 | Cross | |
| 7,767,698 B2 | 8/2010 | Warchol | |
| 7,832,410 B2 | 11/2010 | Hon | |
| 7,992,554 B2 | 8/2011 | Radomski | |
| 8,156,944 B2 | 4/2012 | Hon | |
| 8,365,742 B2 | 2/2013 | Hon | |
| 8,375,957 B2 | 2/2013 | Hon | |
| 8,393,331 B2 | 3/2013 | Hon | |
| 8,430,106 B2 | 4/2013 | Potter et al. | |
| 8,490,628 B2 | 7/2013 | Hon | |
| 8,511,318 B2 | 8/2013 | Hon | |
| 8,752,545 B2 | 6/2014 | Buchberger | |
| 8,689,805 B2 | 8/2014 | Hon | |
| 8,833,364 B2 | 9/2014 | Buchberger | |
| 8,910,640 B2 * | 12/2014 | Sears | F22B 1/28 131/273 |
| 8,948,578 B2 | 2/2015 | Buchberger | |
| 9,609,894 B2 * | 4/2017 | Abramov | A24F 47/008 |
| 9,623,205 B2 | 4/2017 | Buchberger | |
| 10,010,695 B2 | 7/2018 | Buchberger | |
| 10,045,562 B2 | 8/2018 | Buchberger | |
| 2001/0042546 A1 | 11/2001 | Umeda et al. | |
| 2002/0005207 A1 | 1/2002 | Wrenn | |
| 2002/0016370 A1 | 2/2002 | Shytle | |
| 2002/0079309 A1 | 6/2002 | Cox et al. | |
| 2003/0005620 A1 | 1/2003 | Shytle | |
| 2003/0049025 A1 | 3/2003 | Neumann | |
| 2003/0079309 A1 | 6/2003 | Cox | |
| 2003/0106552 A1 | 6/2003 | Sprinkel | |
| 2003/0108342 A1 | 6/2003 | Sherwood | |
| 2003/0200964 A1 | 10/2003 | Blakely | |
| 2003/0202169 A1 | 10/2003 | Liu | |
| 2004/0031485 A1 | 2/2004 | Rustad | |
| 2004/0129793 A1* | 7/2004 | Nguyen | A61M 11/041 239/13 |
| 2004/0210151 A1 | 10/2004 | Tsukashima | |
| 2004/0226568 A1 | 11/2004 | Takeuchi | |

(56) References Cited

U.S. PATENT DOCUMENTS

| | | |
|---|---|---|
| 2005/0063686 A1 | 3/2005 | Whittle |
| 2005/0145260 A1 | 7/2005 | Inagaki |
| 2005/0194013 A1 | 9/2005 | Wright |
| 2005/0204799 A1 | 9/2005 | Koch |
| 2005/0268911 A1 | 12/2005 | Cross |
| 2006/0078477 A1 | 4/2006 | Althouse |
| 2006/0137681 A1 | 6/2006 | Von Hollen |
| 2007/0014549 A1 | 1/2007 | Demarest et al. |
| 2007/0045288 A1 | 3/2007 | Nelson |
| 2007/0062548 A1 | 3/2007 | Horstmann |
| 2007/0102013 A1 | 5/2007 | Adams |
| 2007/0107879 A1 | 5/2007 | Radomsnki |
| 2007/0155255 A1 | 7/2007 | Galauner |
| 2007/0267031 A1 | 11/2007 | Hon |
| 2008/0092912 A1 | 4/2008 | Robinson et al. |
| 2008/0156326 A1 | 7/2008 | Belcastro |
| 2008/0216828 A1 | 9/2008 | Wensley |
| 2008/0241255 A1 | 10/2008 | Rose |
| 2009/0090472 A1 | 4/2009 | Radomski |
| 2009/0095311 A1 | 4/2009 | Han |
| 2009/0188490 A1 | 7/2009 | Han |
| 2009/0241947 A1 | 10/2009 | Bedini |
| 2009/0272379 A1 | 11/2009 | Thorens |
| 2009/0293892 A1 | 12/2009 | Williams |
| 2010/0059070 A1 | 3/2010 | Potter |
| 2010/0065653 A1 | 3/2010 | Potter |
| 2010/0083959 A1* | 4/2010 | Siller ............... A24F 47/006 128/202.21 |
| 2010/0108059 A1 | 5/2010 | Axelsson et al. |
| 2010/0236546 A1 | 9/2010 | Yamada |
| 2010/0242974 A1 | 9/2010 | Pan |
| 2011/0011396 A1 | 1/2011 | Fang |
| 2011/0126848 A1 | 6/2011 | Zuber |
| 2011/0155153 A1 | 6/2011 | Thorens |
| 2011/0192914 A1 | 8/2011 | Ishigami |
| 2011/0226236 A1 | 9/2011 | Buchberger |
| 2011/0277757 A1 | 11/2011 | Terry |
| 2011/0036363 A1 | 12/2011 | Urtsev |
| 2011/0290267 A1 | 12/2011 | Yamada |
| 2011/0297166 A1 | 12/2011 | Takeuchi |
| 2011/0303231 A1 | 12/2011 | Li |
| 2012/0145169 A1 | 6/2012 | Wu |
| 2012/0260927 A1* | 10/2012 | Liu ............... A24F 47/008 131/329 |
| 2012/0285476 A1 | 11/2012 | Hon |
| 2013/0074857 A1 | 3/2013 | Buchberger |
| 2013/0081623 A1 | 4/2013 | Buchberger |
| 2013/0087160 A1 | 4/2013 | Gherge |
| 2013/0142782 A1 | 6/2013 | Rahmel |
| 2013/0192615 A1 | 8/2013 | Tucker |
| 2013/0213419 A1 | 8/2013 | Tucker |
| 2013/0284192 A1 | 10/2013 | Peleg |
| 2013/0333700 A1 | 12/2013 | Buchberger |
| 2013/0340779 A1 | 12/2013 | Liu |
| 2014/0000638 A1* | 1/2014 | Sebastian ............... A24F 47/008 131/328 |
| 2014/0060528 A1 | 3/2014 | Liu |
| 2014/0060554 A1* | 3/2014 | Collett ............... H05B 3/265 131/328 |
| 2014/0060555 A1 | 3/2014 | Chang |
| 2014/0182608 A1* | 7/2014 | Egoyants ............... A24F 47/008 131/328 |
| 2014/0202454 A1 | 7/2014 | Buchberger |
| 2014/0202476 A1* | 7/2014 | Egoyants ............... A24F 47/008 131/329 |
| 2014/0209105 A1* | 7/2014 | Sears ............... A24F 47/008 131/328 |
| 2014/0216485 A1* | 8/2014 | Egoyants ............... A24F 47/008 131/329 |
| 2014/0238396 A1 | 8/2014 | Buchberger |
| 2014/0238423 A1 | 8/2014 | Tucker |
| 2014/0238424 A1 | 8/2014 | Tucker |
| 2014/0261490 A1 | 9/2014 | Kane |
| 2014/0270726 A1* | 9/2014 | Egoyants ............... A24F 47/004 392/386 |
| 2014/0270730 A1 | 9/2014 | DePiano |
| 2014/0283825 A1 | 9/2014 | Buchberger |
| 2014/0286630 A1 | 9/2014 | Buchberger |
| 2014/0299125 A1 | 10/2014 | Buchberger |
| 2014/0338680 A1 | 11/2014 | Abramov |
| 2015/0114411 A1 | 4/2015 | Buchberger |
| 2015/0157055 A1 | 6/2015 | Lord |
| 2015/0181934 A1* | 7/2015 | Lyubomirskiy ....... A24F 47/008 131/329 |
| 2015/0196058 A1 | 7/2015 | Lord |
| 2015/0208728 A1 | 7/2015 | Lord |
| 2016/0073693 A1 | 3/2016 | Reevell |
| 2016/0106154 A1 | 4/2016 | Lord |
| 2016/0106155 A1 | 4/2016 | Reevell |
| 2017/0006916 A1 | 1/2017 | Qiuming |
| 2017/0042245 A1 | 2/2017 | Buchberger |
| 2017/0197043 A1 | 7/2017 | Buchberger |
| 2017/0197044 A1 | 7/2017 | Buchberger |
| 2017/0197046 A1 | 7/2017 | Buchberger |

FOREIGN PATENT DOCUMENTS

| | | |
|---|---|---|
| AT | 510504 | 4/2012 |
| AU | 63913/73 | 6/1975 |
| AU | 63931/73 | 6/1975 |
| CA | 2309376 | 11/2000 |
| CH | 698603 B1 | 9/2009 |
| CN | 2092880 | 1/1992 |
| CN | 2220168 | 2/1996 |
| CN | 1205849 A | 1/1999 |
| CN | 2719043 | 8/2005 |
| CN | 1694765 A | 11/2005 |
| CN | 201238609 | 5/2009 |
| CN | 201375023 | 1/2010 |
| CN | 101648041 A | 2/2010 |
| CN | 101878958 | 11/2010 |
| CN | 202172846 | 3/2012 |
| CN | 102655773 A | 9/2012 |
| CN | 202722498 | 2/2013 |
| CN | 202750708 | 2/2013 |
| CN | 105310114 | 2/2016 |
| CN | 106102863 A | 11/2016 |
| DE | 1950439 | 4/1971 |
| DE | 3148335 | 7/1983 |
| DE | 3218760 | 12/1983 |
| DE | 3936687 | 5/1992 |
| DE | 29719509 U1 | 1/1998 |
| DE | 19630619 | 2/1998 |
| DE | 19654945 | 3/1998 |
| DE | 10330681 | 6/2004 |
| DE | 202006013439 | 10/2006 |
| DE | 202013100606 | 2/2013 |
| EA | 019736 | 5/2014 |
| EA | 022685 | 2/2016 |
| EP | 280262 | 8/1988 |
| EP | 0358002 A2 | 3/1990 |
| EP | 0358114 | 3/1990 |
| EP | 0444553 | 9/1991 |
| EP | 04888488 A1 | 6/1992 |
| EP | 0845220 | 6/1998 |
| EP | 0295122 | 12/1998 |
| EP | 0893071 | 1/1999 |
| EP | 1166814 | 1/2002 |
| EP | 1166847 | 1/2002 |
| EP | 1736065 | 12/2006 |
| EP | 1757921 A2 | 2/2007 |
| EP | 2018886 | 1/2009 |
| EP | 2022349 | 2/2009 |
| EP | 2113178 | 11/2009 |
| EP | 2340729 A1 | 7/2011 |
| EP | 2698070 | 2/2014 |
| EP | 2907397 | 4/2014 |
| EP | 2762019 | 8/2014 |
| EP | 2835062 | 2/2015 |
| FR | 960469 | 4/1950 |
| GB | 25575 | 3/1912 |
| GB | 1313525 | 4/1973 |

(56) References Cited

FOREIGN PATENT DOCUMENTS

| | | |
|---|---|---|
| HK | 1196511 | 12/2014 |
| HK | 1226611 | 10/2017 |
| JP | S57-052456 | 3/1982 |
| JP | S59-106340 | 1/1986 |
| JP | 61-096765 | 5/1986 |
| JP | S61-096763 | 5/1986 |
| JP | 2124081 | 5/1990 |
| JP | H5-103836 | 4/1993 |
| JP | H05-309136 | 11/1993 |
| JP | H6-315366 A | 11/1994 |
| JP | H8-511176 | 10/1995 |
| JP | H08-299862 | 11/1996 |
| JP | 11089551 | 4/1999 |
| JP | 2011518567 | 1/2002 |
| JP | 2004332069 | 11/2004 |
| JP | 2005-538159 | 12/2005 |
| JP | 2005537918 A | 12/2005 |
| JP | 2009-509523 | 3/2009 |
| JP | 2009-537119 | 10/2009 |
| JP | 2012-249854 | 12/2012 |
| KR | 1020050037919 | 4/2006 |
| KR | 20130006714 | 11/2013 |
| RU | 2336001 C2 | 11/2005 |
| RU | 2311859 C2 | 12/2007 |
| RU | 89927 U1 | 12/2009 |
| RU | 94815 U1 | 6/2010 |
| RU | 103281 U1 | 4/2011 |
| RU | 115629 U1 | 5/2012 |
| RU | 122000 U1 | 11/2012 |
| RU | 124120 | 1/2013 |
| RU | 132318 | 9/2013 |
| RU | 2509516 | 3/2014 |
| WO | WO9527412 | 10/1995 |
| WO | WO9632854 | 10/1996 |
| WO | WO9748293 A1 | 12/1997 |
| WO | WO98017131 | 4/1998 |
| WO | WO200009188 | 2/2000 |
| WO | WO200021598 | 4/2000 |
| WO | WO2000050111 | 8/2000 |
| WO | WO2002051468 | 7/2002 |
| WO | WO2002058747 | 8/2002 |
| WO | WO2003028409 A1 | 4/2003 |
| WO | WO 2003/050405 A1 | 6/2003 |
| WO | WO2003083283 A1 | 10/2003 |
| WO | WO 2003/101454 | 12/2003 |
| WO | WO2004/022128 | 3/2004 |
| WO | WO2004022242 | 3/2004 |
| WO | WO2004022243 | 3/2004 |
| WO | WO2005106350 A2 | 11/2005 |
| WO | WO2006082571 | 8/2006 |
| WO | WO 2007/042941 | 4/2007 |
| WO | WO 2007/131449 A | 11/2007 |
| WO | WO2007141668 | 12/2007 |
| WO | WO2008038144 | 4/2008 |
| WO | WO2009015410 | 2/2009 |
| WO | WO2009118085 A1 | 10/2009 |
| WO | WO 2009/132793 A1 | 11/2009 |
| WO | WO2010045670 A1 | 4/2010 |
| WO | WO2010045671 A1 | 4/2010 |
| WO | WO 2011/050943 A1 | 5/2011 |
| WO | WO 2011/109849 A1 | 9/2011 |
| WO | WO 2012/025496 A1 | 3/2012 |
| WO | WO 2013/034453 A1 | 3/2013 |
| WO | WO 2013/034460 A1 | 3/2013 |
| WO | WO 2013/057185 A1 | 4/2013 |
| WO | WO 2013/082173 | 6/2013 |
| WO | WO 2013/098395 A1 | 7/2013 |
| WO | WO2013116558 | 8/2013 |
| WO | WO2013116572 | 8/2013 |
| WO | WO2014130695 | 8/2013 |
| WO | WO2013152873 A1 | 10/2013 |
| WO | WO 2014/012906 | 1/2014 |
| WO | WO2014061477 A1 | 4/2014 |
| WO | WO 2014/140320 A1 | 9/2014 |
| WO | WO 2014/150131 A1 | 9/2014 |
| WO | WO 2015/114328 | 8/2015 |
| WO | WO 2015/165812 | 11/2015 |

OTHER PUBLICATIONS

Chinese Office Action for Chinese Application No. 201480024978.X dated Jan. 18, 2017.
European Search Report for European Application No. 15178588 dated Apr. 14, 2016.
International Preliminary Report on Patentability, dated Apr. 22, 2014, for International Patent Application No. PCT/EP2012/070647, filed Oct. 18, 2012.
International Search Report and Written Opinion for International Application No. PCT/EP2012/003103, dated Nov. 26, 2012.
International Search Report and Written Opinion for PCT/AT2012/000017 dated Jul. 3, 2012.
International Search Report and Written Opinion for PCT/GB2014/051333 dated Jul. 17, 2014.
International Search Report and Written Opinion, International Application No. PCT/GB2014/051332 dated Jul. 21, 2014.
International Search Report and Written Opinion, International Application No. PCT/GB2014/051334 dated Jul. 21, 2014.
IPRP mailed Aug. 5, 2015 for International Application No. PCT/GB2014/051333.
IPRP, International Application No. PCT/GB2014/051332 mailed Nov. 12, 2015.
IPRP, International Application No. PCT/GB2014/051334 mailed Nov. 12, 2015.
Japanese Notice of Reasons for Rejection for Japanese Application No. 2015-137361 dated May 31, 2016.
Russian Search Report for Russian Application No. 2015146843/12 (072088) date completed Apr. 24, 2017.
Russian Office Action, Application No. 2014120213/12, dated Oct. 26, 2016, 7 pages.
Russian Office Action, Application No. 2014120213/12, dated Sep. 22, 2017, 11 pages.
Chinese Office Action, Application No. 201480024988.3, dated Dec. 30, 2016, 26 pages.
Chinese Office Action, Application No. 201480024988.3, dated Sep. 11, 2017, 21 pages.
European Extended Search Report, Application No. 17189951.1, dated Jan. 4, 2018, 8 pages (11 pages with translation).
Plasma polymerization (the company Diener electronic GmbH+Co. KG), www.plasma.de, retrieved on Oct. 17, 2017, 19 pages.
International Preliminary Report on Patentability (WIPO English Translation), dated Aug. 13, 2013 for International Patent Application No. PCT/AT2012/000017, filed Feb. 2, 2012.
Pulmonary Pharmacoloy: Delivery Devices and Medications, dated Sep. 6, 2017, 2 pages, available at www.cdeu.org/cecourses/z98207/ch4.htm.
Dunn P and Reay D, Heat Pipes, 4th edition, 1994, ISBN 0080419038, 14 pages.
Application and File History for U.S. Appl. No. 13/125,343, filed Apr. 21, 2011 inventor Buchberger.
Japanese Notice of Reasons for Rejection dated Sep. 8, 2015 for Japanese Application No. 2014179732.
Japanese Notice of Reasons for Rejection dated Oct. 15, 2013 for Japanese Application No. 2011532464.
Application and File History for U.S. Appl. No. 14/306,831, filed Jun. 17, 2014, inventor Buchberger.
European Search Report for European Application No. 16166656 dated Oct. 11, 2016.
Notice of Opposition Letter from EPO. Opposition against: EP2358418 dated Mar. 1, 2017.
Rudolph G, BAT Cigarettenfabriken GmbH, 1987, The Influence of CO2 on the Sensory Characteristics of the Favor-System, http://legacy.library.ucsf.edu/tid/sla51f00.
Application and File History for U.S. Appl. No. 15/470,078, filed Mar. 27, 2017, inventor Buchberger.
Application and File History for U.S. Appl. No. 15/470,095, filed Mar. 27, 2017, inventor Buchberger.

(56) References Cited

OTHER PUBLICATIONS

International Search Report for International Application No. PCT/AT2009/000413 dated Jan. 25, 2010.
Chinese First Office Action for Chinese Application No. 200980152395.4 dated Dec. 3, 2012.
Chinese Second Office Action for Chinese Application No. 200980152395.4 dated Aug. 20, 2013.
Japanese Reasons for Rejection for Japanese Application No. 2016134648 dated May 23, 2017.
Japanese Decision to Grant, Application No. 2016-134648, dated May 22, 2018, 3 pages (4 pages with translation).
Japanese Office Action, Application No. 2016-564977, dated Dec. 5, 2017, 3 pages (6 pages with translation).
Japanese Search Report, Application No. 2016-864977, dated Oct. 25, 2017, 9 pages (19 pages with translation).
Chinese Office Action, Application No. 201580022356.8, dated Jul. 18, 2018, 8 pages (15 pages with translation).
International Search Report for International Application No. PCT/AT2009/000414 dated Jan. 26, 2010.
Kynol, *Kynol Standard Specifications of Activated Carbon Fiber Products*, 2 pages, as retrieved on Sep. 19, 2013.
Application and File History for U.S. Appl. No. 14/296,803, filed Jun. 5, 2014 inventor Buchberger.
Application and File History for U.S. Appl. No. 15/454,156, filed Mar. 9, 2017, inventor Buchberger.
International Search Report for corresponding International Application No. PCT/GB2015/051213 dated Jul. 16, 2015; 5 pages.
Written Opinion of the International Searching Authority for corresponding International Application No. PCT/GB2015/051213 dated Jul. 16, 2015; 9 pages.
Written Opinion of the International Preliminary Examining Authority for corresponding International Application No. PCT/GB2015/051213 dated Mar. 29, 2016; 10 pages.
International Preliminary Report on Patentability for corresponding International Application No. PCT/GB2015/051213 dated Jul. 14, 2016; 21 pages.
Chinese Search Report, Application No. 201610086101.4, dated Apr. 25, 2018, 1 page.
Chinese Office Action, 201610086101.4, dated May 4, 2018, 3 pages.
Chinese Office Action and Search Report, Application No. 201610371843.1, dated Sep. 30, 2018, 6 pages (11 pages with translation).
Japanese Decision to Grant, Application No. JP2016-134648, dated May 22, 2018, 6 pages.
International Search Report and Written Opinion, Application No. PCT/GB2017/051139, dated Aug. 9, 2017, 16 pages.
International Preliminary Report on Patentability, Application No. PCT/GB2017/051139, dated Aug. 6, 2018, 8 pages.
Application and File History for U.S. Appl. No. 15/997,113, filed Jun. 4, 2018, Inventor: Buchberger.
Application and File History for U.S. Appl. No. 14/594,065, filed Jan. 9, 2015, Inventor: Buchberger.
Application and File History for U.S. Appl. No. 16/096,554, filed Oct. 25, 2018, Inventor: Fraser.
Company Filtrona Richmond, Inc., www.filtronaporoustechnologies.com, dated Nov. 19, 2008, 1 page.
Japanese Search Report, Application No. 2011-532464, dated Sep. 19, 2013, 116 pages.
Japanese Search Report, Application No. 2014-179732, dated Aug. 25, 2015, 5 pages.
Japanese Search Report, Application No. 2016-134648, dated Apr. 14, 2017, 26 pages.
Russian Decision to Grant, Application No. 2011120430/14, dated Apr. 1, 2014, 10 pages.
European Search Report, Application No. 18205608.5, dated Jul. 12, 2019, 7 pages.
European Communication, Application No. 17189951.1, dated Jan. 25, 2019, 4 pages.
Japanese Office Action and Search Report, Application No. 2018-088088, dated Feb. 28, 2019, 25 pages.
Japanese Decision to Grant, Application No. 2011-532464, dated Aug. 5, 2014, 3 pages (6 pages with translation).
Chinese Notification to Grant Patent, Application No. 201610086101.4, dated Oct. 25, 2018, 2 pages.
Russian Search Report, Application No. 2018137501, dated Apr. 29, 2019, 12 pages.
Russian Search Report, Application No. 2018137583/12, dated Jun. 24, 2019, 2 pages.
Notice of Opposition on behalf of JT International S.A., Opposition against EP 3117860 (Application No. 16166656.5), dated Oct. 30, 2019, 39 pages.
Australian Examination Report, Application No. 2017256084, dated Nov. 20, 2019, 3 pages.

\* cited by examiner

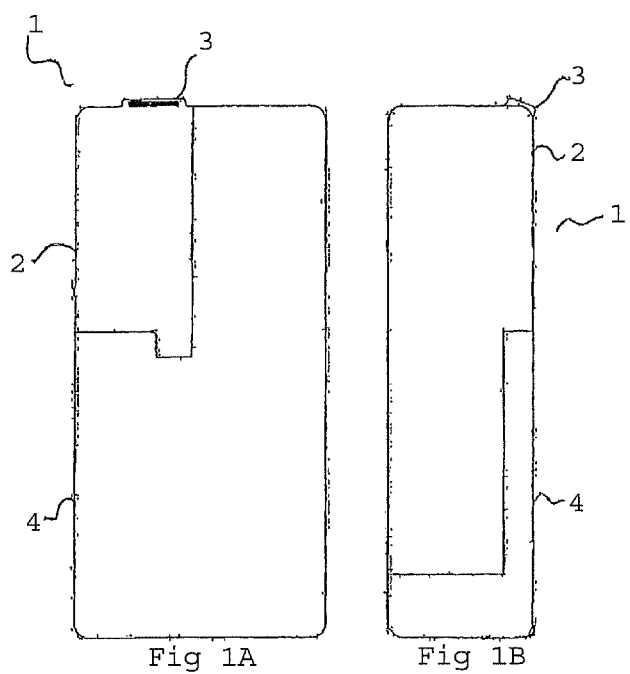
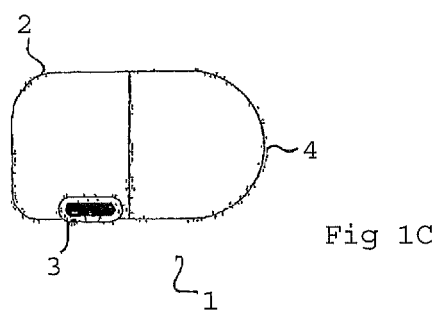

AEROSOL FORMING COMPONENT

CROSS-REFERENCE TO RELATED APPLICATIONS

The present application is a National Phase entry of PCT Application No. PCT/GB2015/051213, filed on 27 Apr. 2015, which claims priority to GB Patent Application No. 1407426.4, filed on 28 Apr. 2014, which are hereby fully incorporated herein by reference.

TECHNICAL FIELD

The disclosure relates to an aerosol forming component and an aerosol delivery device comprising such an aerosol forming component. The disclosure also relates to a method for volatilizing liquids from an aerosol delivery device.

BACKGROUND

The use of a heating component to effect volatilization of a liquid material from an aerosol delivery device for subsequent inhalation by a user is known. Such devices comprise a single heating element or a heating component composed of multiple heating elements which are activated simultaneously. However, the use of such heating elements has disadvantages.

Liquid material intended for use in an aerosol delivery device which comprises a heating element typically comprises several constituents having variable volatilities. As a result, when the heating element(s) is activated, the more volatile constituents vaporize before the less volatile constituents. This can result in asynchronous release of constituents from the aerosol delivery device, and deposition of the more volatile constituents in the aerosol delivery device, mouth cavity or throat of the user.

For example, nicotine-containing solution for use in an aerosol delivery device as an alternative to the use of a smoking article typically comprises water, which has a boiling point of 100° C.; nicotine, which has a boiling point of 247° C.; and glycerol, which has a boiling point of 290° C. Upon contact with an activated heating element, the water, being the most volatile, will vaporize first, followed by the nicotine, and then the glycerol. Depending on the composition of the liquid material at least a portion, most or all of the nicotine may be vaporized together with the water. This asynchronous release of substances results in a relatively high concentration of nicotine in the gas and particle phase of the generated condensation aerosol in an early stage of the inhalation, yet most of this nicotine will never reach the lungs of the user, but rather will be deposited in the aerosol delivery device, mouth cavity or throat of the user as a result of dissociation from the glycerol.

SUMMARY

According to an aspect of the present disclosure, there is provided an aerosol forming component for volatilizing a liquid in an aerosol delivery device, comprising a first aerosol-forming member configured to be heated up to a first operating temperature and thereafter to a second higher operating temperature, and a second aerosol-forming member configured to be heated up to at least the first operating temperature as the first aerosol-forming member reaches the second higher operating temperature so that liquid volatilized from the two aerosol-forming members mix with one another.

In one embodiment, the first aerosol-forming member may reach the second operating temperature substantially at the same time as the second aerosol-forming member reaches the first operating temperature such that liquid volatilized from the two aerosol-forming members mix with one another.

In one embodiment, the aerosol-forming members may be configured to have different heating rates, such that by activating the aerosol-forming members simultaneously, the first aerosol forming member reaches the second operating temperature substantially at the same time as the second aerosol-forming member reaches the first operating temperature.

In another embodiment, the first aerosol-forming member may be activated prior to activation of the second aerosol-forming member such that the first aerosol forming member reaches the second operating temperature substantially at the same time as the second aerosol-forming member reaches the first operating temperature.

In yet another embodiment, the first aerosol-forming member may be located upstream of the second aerosol-forming member with respect to the flow of air through the aerosol delivery device in use.

In an alternative embodiment, the first and second aerosol-forming members may be located next to each other in a direction transverse to the flow of air through the aerosol forming component in use.

In one embodiment, the aerosol forming component may further comprise a liquid for volatilization, wherein the liquid comprises one or more aerosol generating means and one or more low boiling point fraction(s).

The liquid may comprises nicotine and/or one or more volatile acids.

In one embodiment, the aerosol generating means are volatilized from the first aerosol-forming member as it reaches the second operating temperature and the one or more low boiling point fraction(s) are volatilized from the second aerosol-forming member when it reaches its first operating temperature such that the one or more low boiling point fraction(s) settles on the aerosol generating means.

According to another aspect, there is provided an aerosol delivery device comprising an aerosol forming component as described above.

The aerosol delivery device may comprise a housing comprising an air inlet and an air outlet, an aerosol chamber in fluid communication with the air inlet and the air outlet, and a power source to which the aerosol forming members are electrically connected and a controller for controlling activation of the aerosol-forming members.

According to yet another aspect of the invention there is provided a method for volatilizing a liquid within an aerosol delivery device comprising a first and a second aerosol-forming member, the method comprises heating up the first aerosol-forming member to a first operating temperature and thereafter to a second higher operating temperature, and heating up the second aerosol-forming member to at least the first operating temperature as the first aerosol-forming member reaches the second higher operating temperature so that liquid volatilized from the aerosol-forming members mix with one another.

The method may further comprise heating up the first aerosol-forming member to a first operating temperature and thereafter to a second higher operating temperature, and heating up the second aerosol-forming member so that it reaches the first operating temperature substantially at the same time as the first aerosol-forming member reaches its second operating temperature.

In one embodiment, the aerosol-forming members are configured to have different heating rates, and the method comprises activating the aerosol-forming members simultaneously and the first aerosol forming member reaches the second operating temperature substantially at the same time as the second aerosol-forming member reaches the first operating temperature.

In another embodiment, the first aerosol-forming member is activated prior to activation of the second aerosol-forming member such that the first aerosol forming member reaches the second operating temperature substantially at the same time as the second aerosol-forming member reaches the first operating temperature.

BRIEF DESCRIPTION OF THE DRAWINGS

Embodiments of the disclosure will now be described, by way of example only, with reference to the accompanying drawings, in which:

FIG. 1A shows a front view of an aerosol delivery device according to the disclosure.

FIG. 1B shows a side view of the aerosol delivery devices.

FIG. 1C shows a top view of the aerosol delivery device.

DETAILED DESCRIPTION

Figure 2:
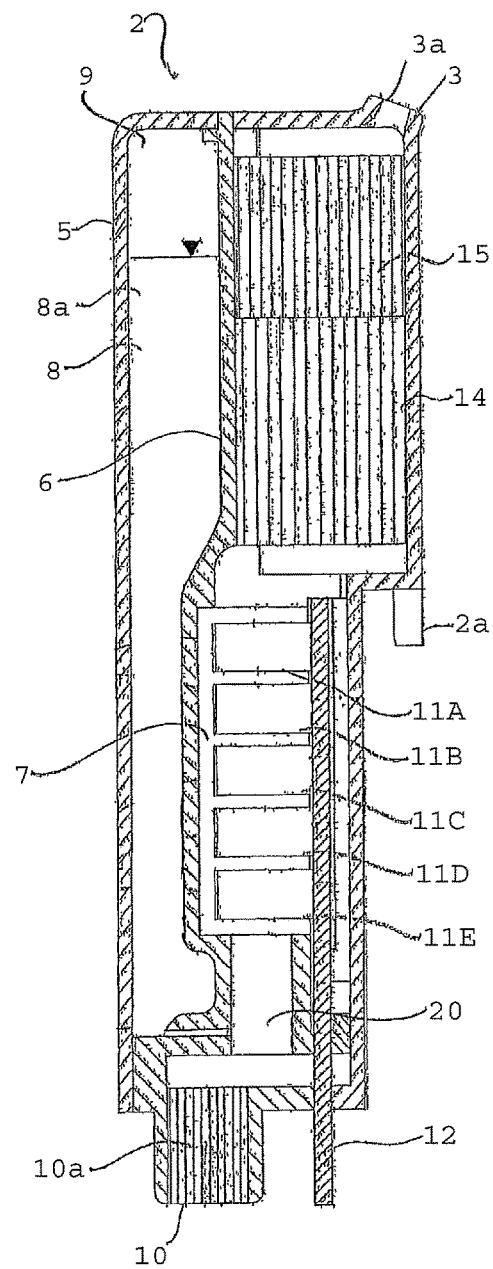
FIG. 2 show a cross-sectional side view of an aerosol delivery device component according to the disclosure.

The term "aerosol generating means" as used herein means a substance which rapidly creates or promotes an aerosol upon reaching volatilization temperature.

The term "capillary structure" as used herein refers to any structure through which liquid can travel as a result of capillary action.

The term "upstream" as used herein is with reference to the flow of air and aerosol through the aerosol delivery device in use.

The term "activated" as used herein with regard to an aerosol-forming member means the initiation of supply of an electric current to the aerosol-forming member so that it heats up to an operating temperature.

The term "operating temperature" as used herein means a temperature at which at least one of the constituents of a liquid material is volatilized upon contact with, or being placed in close proximity to the activated aerosol-forming member.

The term "sequentially" as used herein is with reference to the supply of electrical energy from an energy store to the aerosol-forming members in a serial fashion, so that the first aerosol-forming member (i.e. the aerosol-forming member located most upstream with respect to the flow of air through the aerosol delivery device in use) is activated first; followed by activation of the second aerosol-forming member, which is located downstream of the first member; followed by activation of the third aerosol forming member, which is located downstream of the second member, etc.

The term "aerosol delivery device" as used herein refers to a device capable of generating and delivering aerosol to a user.

The term "capillary gap" as used herein is considered to be any gap that brings about a liquid transport by virtue of the capillary action of its boundary walls.

Referring now to FIGS. 1A, 1B and 1C, an embodiment of an aerosol delivery device 1 according to the invention is shown from different views. The size and form of such aerosol delivery device 1 may be configured so that they can be easily and conveniently handled by the user, for example, the aerosol delivery device 1 may have a volume of around 10-50 $cm^3$.

The aerosol delivery device 1 may be of any design which is suitable for creation and delivery of vaporized liquid material.

As shown in FIGS. 1A to 1C, the aerosol delivery device 1 comprises an aerosol delivery device component 2 with a mouthpiece 3, an energy store component 4 having a power source and a controller (not shown) connected to an electrical circuit (not shown). The aerosol delivery device component 2 is shown in more detail in FIG. 2 and it is configured to be detachably attached to the energy store component 4 by the use of a snap-in hook 2a for insertion into a corresponding lug on the energy store component (not shown). However, it should be understood that any means of achieving this may be used, for example a snap connector comprising one or more snap-in hooks and corresponding latching lugs, or a tongue and groove arrangement.

The power source of the energy store component 4 may be a cylindrical lithium ion cell of size 18650 with a storage capacity of 1650 mAh and a current load of up to 30 A. Any power source which is suitable for activating aerosol-forming members located in the aerosol delivery device component 2 and effecting volatilization of the liquid material may be used, such as one or more batteries. Furthermore, aerosol delivery devices of smaller size may use flat lithium polymer pouch cells.

The controller of the energy store component 4 controls the flow of electric current from the power source to the aerosol delivery device component 2 as described below.

The aerosol delivery device component 2 comprises a housing 5 as seen in FIG. 2. A space inside the housing is divided by a partitioning wall 6 into an aerosol chamber 7 and a liquid reservoir 8. The liquid reservoir 8 contains a liquid material 8a, and an air cushion 9. In FIG. 2 the liquid reservoir 8 has a capacity of around 4 $cm^3$, and the liquid charge is around 3.6 mls, however it should be understood that the present disclosure is not limited to these parameters.

The liquid material may comprise one or more stimulants, such as nicotine or one or more therapeutics. The stimulant or therapeutic may be included in the liquid material in the amount of 0.1-5%; 0.5-2%; 0.5-5%; 0.8-3%; or 1-2% by weight.

The liquid material may additionally comprise one or more aerosol generating means, such as polyhydric alcohols, glycerol, propylene glycol, triethylene glycol, triethyl citrate or high boiling point hydrocarbons. The aerosol generating means may be included in the liquid material in the amount of 5-95%, 5-15%; 6-12%; 8-10% or around 10% by weight.

The liquid material may additionally comprise one or more low boiling point fractions, such as water or ethanol. Such fractions can reduce viscosity of the liquid material, and may comprise 5-95% or more than 50%, 60%, 70%, 80%, 82% or 84% by weight of the liquid material in total.

The liquid material may comprise one or more additional constituents, such as lactic acid, succinic acid, levulinic acid, benzoic acid, phenyl acetic acid, acetic acid, formic acid. When the liquid material comprises nicotine, such an acid may be added to protonate the nicotine.

The liquid material may further comprise one or more flavorants. As used herein, the terms "flavor" and "flavorant" refer to materials which, where local regulations permit, may be used to create a desired taste or aroma in a product for adult consumers. In some embodiments, the flavor or flavorant may be menthol, citrus, vanillin, aniseed, transanethole, benzaldehyde or acetylaldehyde.

Referring again to FIG. 2, an inlet passage created by a tubular structure 10 fluidly communicates with the aerosol chamber 7 via a nozzle 20, and the other side of the aerosol chamber 7 fluidly communicates with an outlet aperture 3a formed in the mouthpiece 3. The inlet passage is ideally located at the opposite end of the aerosol delivery device 1 to the mouthpiece 3, as this prevents entry of rainwater in use. The inlet passage may comprise a flow restrictor 10a such as a fiber composite (such as that provided by Filtrona Fibertec GmbH) similar to that found in the filter of a cigarette, which imparts to the user a feeling similar to that of a drawing on a cigarette upon inhalation through the aerosol delivery device.

An aerosol forming component is located in the aerosol chamber 7. The aerosol forming component comprises at least two aerosol-forming members. In FIG. 2, the aerosol forming component is composed of five aerosol-forming members, 11A-11E. The nozzle 20 directs air inhaled by the user via the inlet passage pass or across the five aerosol-forming members 11A-11E.

The aerosol-forming members 11A-11E may be of any design which is suitable for effecting vaporization of the liquid material 8a in an aerosol delivery device upon application of electrical input.

The aerosol forming-members 11A-11E may also be any shape suitable for purpose, and may be shaped so as to increase the surface area available for volatizing or evaporating the liquid material 8a. In one embodiment, the aerosol-forming members 11A-11E may comprise a sheet of material having a single layer that is configured to wick and heat the liquid material 8a. Thus, the sheet of material can absorb liquid material from the solution reservoir 8 and thereafter heat it up so that it vaporizes or evaporates and forms a vapor. The sheet of material is sheet-like in nature and may have a rectangular shape. However, it should be understood that the sheet of material may be of any shape, for example, circular, oval or square. The sheet of material comprises two opposing major surfaces. The sheet of material may comprise an open-pored structure, foam structure or interconnecting network of pores, all of which form a capillary structure.

The aerosol-forming members 11A-11E may be made of a homogenous, granular, fibrous or flocculent sintered metal(s) so as to form said capillary structure. In another embodiment, the aerosol-forming members 11A-11E comprise an open-pored metallic foam which also forms a capillary structure. Alternatively, the aerosol-forming members 11A-11E may be formed from a mesh material providing a capillary structure. The aerosol-forming members 11A-11E may be made of stainless steel such as AISI 304 or AISA 316 or heat conducting alloys such as NiCr alloys. The capillary structure is exposed at least on one of the major surfaces of each aerosol-forming member 11A-11E. For example, the aerosol-forming members 11A-11E may be formed with a capillary structure that extends completely throughout the aerosol-forming members 11A-11E such that it is exposed on both major surfaces of the sheet of material of each aerosol-forming member 11A-11E. In another embodiment, the aerosol-forming members 11A-11E are configured such that the capillary structure does not extend completely throughout each of the aerosol-forming members 11A-11E. For example, the capillary structure may only be exposed on one of the major surfaces or a section of both or either of the major surfaces of each aerosol-forming member 11A-11E.

The material from which the aerosol-forming members 11A-11E are formed is heatable in that it comprises sufficient electrical resistivity so that when an electric current is passed through, the aerosol-forming member heats up to a temperature sufficient to cause the liquid material 8a held in the capillary structure to evaporate or vaporize. In the embodiments wherein the sheet of material of each aerosol-forming member 11A-11E comprises a single layer as described above, the aerosol-forming members 11A-11E can be considered to comprise a heating element formed with a capillary structure such that the heating element and the capillary structure are integrated and form a single entity or unit.

In the above described embodiments wherein the sheet of material of each aerosol-forming member 11A-11E comprises a single layer configured to wick and heat a solution, the sheet of material can be described as comprising a heating element and a wick that are arranged in the same surface.

In an alternative un-illustrated embodiment, the aerosol-forming members comprise a sheet of material that is sheet-like in nature and formed from a plurality of layers. For example, each aerosol-forming member may comprise a first heatable layer acting as a heating element. This first layer is formed from a material that is configured to be heated up. Each aerosol-forming member may further comprise a second layer formed with an open-pored structure, foam structure, mesh structure, or interconnecting network of pores, all of which form a capillary structure. The capillary structure enables each aerosol-forming member to wick or absorb a liquid material. This second layer may be made of a homogenous, granular, fibrous or flocculent sintered metal(s) all of which form said capillary structure. The aerosol-forming members may be made of stainless steel, oxidized metals, glass, ceramic, carbon and/or cotton. In all these embodiments, the second layer acts as a wick.

The first layer (heating element) and the second layer (wick having a capillary structure) of each aerosol-forming member are laid on top of each other so as to form a sheet of material having two opposing major surfaces, wherein the capillary structure is exposed on one of the major surfaces.

In an alternative un-illustrated embodiment, the sheet of material of each aerosol-forming member comprises a third layer that is similar to the second layer in that it comprises a capillary structure. The second and the third layers of each aerosol-forming member sandwich the first layer such that the capillary structure is exposed on both major surfaces of the sheet of material of each aerosol-forming member.

In the embodiments wherein the sheet of material of each aerosol-forming member is formed from a plurality of layers as described above, the first layer acting as the heating element and the second and/or third layer(s) acting as the wick are parallel and connected to each other. The layers may be connected to each other by mechanical or chemical means. In one embodiment, the layers are sintered to one another.

The sheet of material of each aerosol-forming member according to any of the above described embodiments has thickness or depth that falls within the range of 20-500 µm. Alternatively, the thickness falls within the range of 50 to 200 µm. The thickness or depth should be understood as meaning the distance between the major surfaces of the sheet of material.

Figure 4:
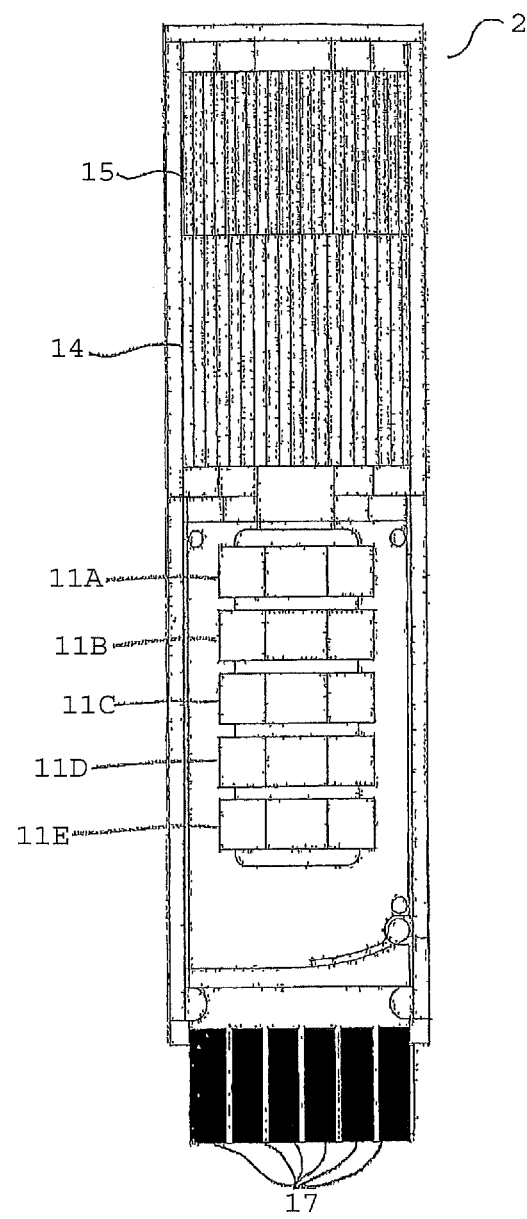
FIG. 4 shows a front planar view of the aerosol delivery device component partially without a housing.

The opposing free ends of each aerosol forming member 11A-11E is mounted onto, or in connection with, a support plate 12, and arranged so that the aerosol forming members 11A-11E extend into the aerosol chamber 7 as can be seen in FIG. 2. Thus, a major portion of each aerosol-forming member 11A-11E is suspended in the aerosol chamber 7. The support plate 12 may be a printed circuit board electrically connecting each aerosol-forming member to the battery in the energy store component 4 so that each aerosol-forming member 11A-11E can be selectively activated. This is achieved by an end portion of the support plate 12 forming electrical connectors 17 which are configured to slot into a corresponding electrical socket (not shown) of the energy store component 4. As can be seen in FIG. 4, the aerosol delivery device component 2 comprise six electrical connectors 17, one of which is an earth, with the remaining five connectors being capable of each activating one of the five aerosol-forming members 11A-11E. The electrical socket (not shown) of the energy store component 4 is electrically connected to the battery (not shown).

Figure 3:
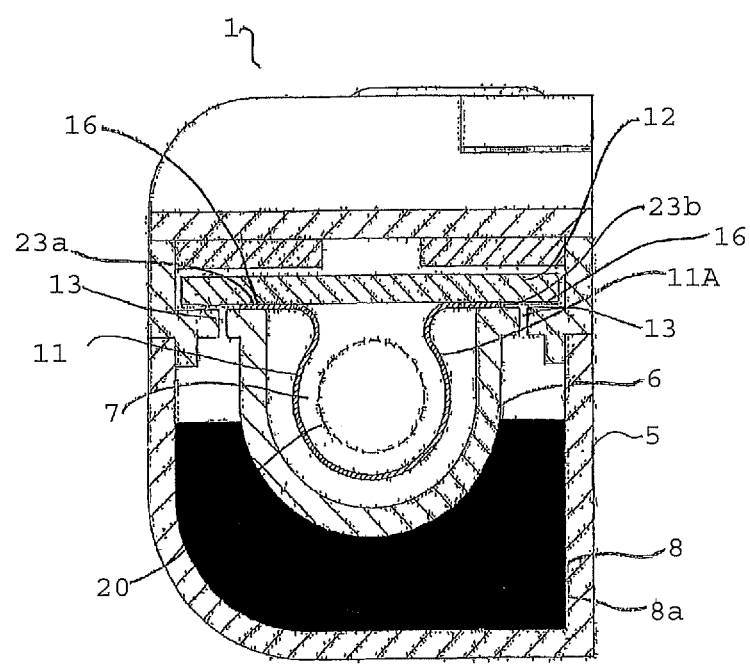
FIG. 3 shows a cross-sectional view of the aerosol delivery device component transverse to the plane of view of FIG. 2.

FIG. 3 shows a cross-sectional view of the aerosol delivery device component 2 according to the invention. As can be appreciated from FIG. 3, the aerosol forming members 11A-11E are curved or bent such that they have an omega-shaped (Ω-shaped) cross-section. Each aerosol forming member 11A-E has opposing ends, 23a and 23b. The opposing ends 23a and 23b are mounted to the support plate 12 so that the aerosol forming members 11A-11E extend into the aerosol chamber 7. The ends 23a, 23b are sandwiched between the support plate 12 and the partitioning wall 6, thereby creating gaps between the support plate 12 and the partitioning wall 6 proximate to the ends 23a and 23b of each aerosol-forming member. These gaps have sufficient width so as to provide a capillary effect, and thus are referred to as capillary gaps 16. Supply apertures 13 are formed in the partitioning wall 6 such that the liquid reservoir 8 and capillary gaps 16 are in fluid communication.

Operation of the aerosol delivery device will now be described with reference to the drawings in FIGS. 1 to 4.

The coupling of the aerosol delivery device component 2 to the energy store component 4 by the user is registered by the controller (not shown), which may result in certain preparatory operations, such as activating one or more of the aerosol-forming members 11A-11E with the object of supplying them with fresh liquid material. Once completed, the controller may be configured to operate a light emitting diode (not shown) so as to indicate to the user that the aerosol delivery device 1 is ready for use.

The aerosol delivery device 1 may then be activated as a result of the user inhaling through the device. This can be achieved by a pressure sensor or flow sensor located in the air passage of the aerosol delivery device 1. Alternatively, the user may activate the aerosol delivery device 1 manually, by depressing a button or other activation mechanism (not shown) on the aerosol delivery device 1.

In either case, activation of the aerosol delivery device 1 results in the controller activating the aerosol forming members 11A-11E in a differential fashion by operating the battery so that it supplies an electric current to the aerosol-forming members 11A-11E via the printed circuit board. As the controller activates each aerosol-forming member 11A-11E an electric current flows through the selected aerosol-forming members such that they each increase in temperature. The controller may operate a transistor located in the energy store component 4 so as to control the flow of electric current to the aerosol-forming members 11A-11E.

Each aerosol forming member is heated for a period of time during activation, the duration of which depends upon the specifications of the aerosol forming members, and on the quantity and composition of the liquid material to be vaporized. In some embodiments, the heating period is between 1 and 1.8 seconds, less than 1 second, less than 0.8 second or less than 0.5 second.

The operating temperature of the aerosol-forming members 11A-11E will depend upon the composition of the liquid material 8a to be vaporized, or more specifically, upon the boiling points of the constituents of the liquid material 8a. It is also envisaged that the operating temperature may rise stepwise during the heating period when the constituents of the liquid material 8a has different boiling points. For example, if the liquid material comprises water, nicotine and glycerol, the aerosol delivery device 1 may be configured such that the operating temperature may rise from ambient temperature to a first operating temperature of approximately 100-140° C., and thereafter the operating temperature may rise to a second operating temperature of approximately 290-330° C.

In one embodiment, the aerosol delivery device 1 is configured such that the aerosol-forming members 11A-11E are deactivated, i.e. the controller stops the battery from supplying an electric current to the aerosol-forming members, before all liquid material 8a held in the capillary structure of each aerosol-forming member have been vaporized so as to avoid their capillary structure from drying out which could result in a temperature runaway and overheating of the aerosol-forming members.

It is envisaged that the aerosol delivery device may be configured such that the operating temperature(s) differs from one inhalation or puff to another. This configuration is suitable if the composition of the liquid material changes from one inhalation or puff to another. The composition of the liquid material 8a may change from one inhalation or puff to another due to localized vaporization effects occurring during refill of liquid material into the capillary structure after the aerosol-forming members have been activated. These vaporization effects cause the aerosol-forming members to cool down quickly as heat is consumed to vaporize the liquid material 8a.

The electric current is supplied from the battery to each aerosol forming member, in a serial fashion, wherein the first (most upstream) aerosol forming member 11E is activated, followed by activation of the second aerosol forming member 11D (i.e. the aerosol forming member located immediately downstream to the first aerosol forming member), etc. This configuration enables less volatile constituents, for example aerosol generating means such as glycerol which has a relatively high boiling point, vaporized by the first aerosol-forming member 11E to interact with more volatile constituents, for example water or nicotine having a lower boiling point, vaporized by the second aerosol-forming member 11D as will now be described in more detail.

The first aerosol-forming member 11E is activated such that its temperature increases to a first operating temperature causing the more volatile constituents to vaporize from the capillary structure of the first aerosol-forming member 11E. Thereafter, the temperature of the first aerosol-forming member 11E is increased to a higher second operating temperature such that aerosol generating means which is less volatile than the other constituents of the liquid material 8a is vaporized. When the vaporized aerosol generating means has vaporized it mixes with ambient air drawn in by the user into the aerosol chamber 7, and condenses so as to form an aerosol. The formed aerosol travels across the second aerosol-forming member 11D due to the air flow generated by the user inhaling. The second aerosol-forming member 11D is activated after the first aerosol-forming member 11D such that the temperature of the second aerosol-forming member 11D increases to the first operating temperature substantially at the same time as the first aerosol-forming member 11E reaches its second operating temperature. This has the effect that the aerosol formed by the first aerosol-forming member 11E passes over the second aerosol-forming member 11D as the more volatile constituents are being vaporized or has just been vaporized from the second aerosol-forming member 11D. The vapor of the more volatile constituents of the second aerosol-forming member 11D is directed towards the aerosol formed from the first aerosol-forming member 11E causing the vapor of the more volatile constituents to condense onto the aerosol formed by the first aerosol-forming member 11E. The remaining aerosol-forming members 11C, 11B, 11A are activated in a serial or sequential fashion respectively so as to achieve the same effect. Advantageously, the amount of more volatile constituents condensing on structural walls and internal constituents of the aerosol delivery device is reduced compared those aerosol delivery devices known from the prior art.

An example will now be described of the above configuration wherein the liquid material comprises water, nicotine and glycerol. The first aerosol-forming member 11E is activated and heated up passed a first operating temperature of 100-140° C. towards a second operating temperature close to the boiling point of glycerol, 290-330° C. so that all constituents of the liquid material vaporize. As glycerol has a higher boiling point than nicotine and water, it will vaporize last. The vapor of glycerol condenses as it cools down and mixes with ambient air drawn in by the user into the aerosol chamber 7 so as to form aerosol glycerol particles. The aerosol glycerol particles then travel with the air flow generated by the user inhaling.

The second aerosol-forming member 11D is activated after the first aerosol-forming member 11E such that it is heated up to the first operating temperature close to the boiling point of water and nicotine 100-140° C. The second aerosol-forming member 11D is activated after the first aerosol-forming member 11E such that the temperature of the second aerosol-forming member 11D increases to the first operating temperature substantially at the same time as the first aerosol-forming member 11E reaches its second operating temperature. Thus, water and nicotine vaporize from the second aerosol-forming member 11D as aerosol glycerol particles from the first aerosol-forming member 11E passes over the second aerosol-forming member 11D. This causes the vapor of water and nicotine from the second aerosol-forming member 11D to condense onto the aerosol glycerol particles vaporized from the first aerosol-forming member 11E. After most of the water and nicotine have been vaporized from the second aerosol-forming member 11D it is heated up further to the second operating temperature close to the boiling point of glycerol, 290-330° C., so that glycerol vaporizes and thereafter condenses so as to form aerosol glycerol particles. The aerosol glycerol particles of the second aerosol-forming member 11D mixes with the aerosol glycerol particles of the first aerosol-forming member 11E as the user inhales so as to form a relatively enriched air flow of aerosol glycerol particles. The air flow enriched with aerosol glycerol particles travels towards the third aerosol-forming member 11C as the user inhales.

The third aerosol-forming member 11C is activated after the second aerosol-forming member 11D to the first operating temperature close to the boiling point of water and nicotine 100-140° C. The third aerosol-forming member 11C is activated after the second aerosol-forming member 11D such that the temperature of the third aerosol-forming member 11C increases to the first operating temperature substantially at the same time as the second aerosol-forming member 11D reaches its second operating temperature. Thus, water and nicotine vaporize from the third aerosol-forming member 11C as aerosol glycerol particles from the first and second aerosol-forming member 11E, 11D pass over the third aerosol-forming member 11C. This causes the vapor of water and nicotine from the third aerosol-forming member 11C to condense onto the aerosol glycerol particles of the first and second aerosol-forming member 11E, 11D. The third aerosol-forming member 11C is then heated up to the second operating temperature and the remaining aerosol-forming members 11B and 11A are activated thereafter in a similar serial fashion.

The aerosol formed by the aerosol forming component as described above is then drawn through a cooler 14, see FIG. 2, as the user continues to inhale so as to cool down the aerosol and to reduce the vapor pressure of the aerosol vapor phase. The cooler 14 can comprise a pore body which is substantially permeable to particles of the aerosol formed. Suitable materials include porous wadding, fleece-like synthetic material (such as Viledon® Filtermatten) synthetic non-wovens manufactured from polyolefin or polyester fibers, or an open-cellular foam material. The pore body may also comprise a regenerator material. Suitable materials have a relatively large surface or heat exchange surface which is capable of absorbing a large amount of heat rapidly without substantial flow losses. Examples include metal wool, metal chips, metal mesh, wire knits, open cell metal foams and fills made from metallic or ceramic granular material such as aluminum granules. Fills of activated charcoal granules could be used as an alternative. Thereafter, the aerosol passes through an absorber 15. The absorber may comprise an open-pore structure which may be similar to the cooler 14. The absorber 15 is intended to absorb condensate deposits from the vapor phase. The absorber material may comprise one or more absorbents such as citric acid which is binding the nicotine.

Flavorings such as menthol may be added to the cooler 14 and/or absorber 15. The cooler 14 and the absorber 15 are configured to refine the aerosol formed by the aerosol generating component to an extent that makes the aerosol more enjoyable to the user.

Finally, the aerosol is drawn into the mouth of the user.

After one inhalation or puff, the controller may prevent the aerosol forming component from being immediately activated so as to allow the aerosol forming members 11A-11E to cool down and replenish the aerosol forming members with liquid material 8a. This period may last for a few seconds, and may be indicated to the user by, for example, a light emitting diode.

Providing an aerosol forming component composed of two or more aerosol forming members wherein the aerosol-forming member most upstream member is activated prior to the second (and any subsequent) aerosol-forming member, improves aerosol formation process as a larger amount of more volatile constituents such as nicotine is carried by the aerosol particles. Differential activation of the aerosol forming members 11A-11E creates a temperature gradient along the aerosol forming component, akin to the temperature gradient that inherently occurs between the distillation zone and burning tip of a smoking article. This results in improved volatilization of the liquid material, and as a result, less volatile constituents of the material are vaporized approximately synchronously with the more volatile constituents. This has the benefit of avoiding or reducing condensation, and therefore deposition, of the more volatile constituents in the aerosol delivery device, mouth cavity or throat of the user.

It should be understood that the present disclosure is not limited to the aerosol forming component comprising a plurality of aerosol-forming members activated sequentially.

In another un-illustrated embodiment, the aerosol-forming members are configured to be activated simultaneously. In such an embodiment the aerosol-forming members are configured to have different heating rates. This may be achieved by forming the aerosol-forming members out of different materials. The aerosol-forming member most upstream is then configured to have the highest heating rate and the heating rate of each aerosol-forming member decreases in a downstream direction. When activating all aerosol-forming members simultaneously, the aerosol-forming members reach the first operating temperature in a serial fashion and the second operating temperature in a serial fashion in a direction of the airflow due to the decrease in heating rates. This has a similar effect to that described with reference to FIGS. 1A to 4 in that when activating all aerosol-forming members simultaneously a first aerosol-forming member is heated up to a first operating temperature and thereafter to a second higher operating temperature, and a second aerosol-forming member located downstream from the first aerosol-forming member with respect to the airflow is heated up to the first operating temperature at substantially the same time as the first aerosol-forming member reaches the second operating temperature so that liquid volatilized from the aerosol-forming members mix with one another.

Although in the embodiments described above the aerosol-forming members are located one after another in the direction of the airflow such that one is more upstream than another, the present disclosure is not limited to such an arrangement. For example, in an un-illustrated embodiment, the aerosol forming component comprise a plurality of aerosol-forming members located next to each other in a direction transverse to the air flow, in other words one aerosol-forming member is not upstream or downstream relative to another aerosol-forming member. In such an embodiment, at least one of the aerosol-forming members is configured to be activated prior to another aerosol-forming member such that the at least one aerosol-forming member reaches the second operating temperature substantially at the same time as the other aerosol-forming member reaches the first operating temperature so that liquid volatilized from the aerosol-forming members mix with one another.

In yet another alternative un-illustrated embodiment, the aerosol forming component comprise a plurality of aerosol-forming members that are located next to each other in a direction transverse to the air flow. The aerosol-forming members are configured to comprise different heating rates such that when activating the aerosol-forming members simultaneously one aerosol-forming member reaches the second operating temperature substantially at the same time as another aerosol-forming member reaches the first operating temperature so that liquid volatilized from the aerosol-forming members mix with one another.

It should be understood that the embodiments of the aerosol forming component according to the present disclosure improve the aerosol formation process as a larger amount of more volatile constituents such as nicotine is carried by the aerosol particles. The aerosol-forming members being heated to the operational temperatures at different time points creates a temperature gradient within the aerosol forming component, akin to the temperature gradient that inherently occurs between the distillation zone and burning tip of a smoking article. This results in improved volatilization of the liquid material, and as a result, less volatile constituents of the material are vaporized approximately synchronously with the more volatile constituents. This has the benefit of avoiding or reducing condensation, and therefore deposition, of the more volatile constituents in the aerosol delivery device, mouth cavity or throat of the user.

In the embodiments according to the present disclosure, one aerosol-forming member is described to reach a second operating temperature at substantially the same time as another aerosol-forming member reaches a first operating temperature. "Substantially at the same time" is to be understood as a period of time that allows for the liquid vaporized from one aerosol-forming member as it reaches the second temperature to mix with liquid vaporized from another aerosol-forming member as it reaches the first operating temperature. The period of time may be less than 1 second (s), 0.75 s, 0.5 s, 0.1 s, 75 ms or 50 ms.

It should also be understood that one aerosol-forming member reaches a second operating temperature at substantially the same time as another aerosol-forming member reaches a first operating temperature during a single puff, drag or inhalation by the user or during one activation cycle.

In order to address various issues and advance the art, the entirety of this disclosure shows by way of illustration various embodiments in which that which is claimed may be practiced and provide for superior aerosol forming components, aerosol delivery devices and methods of volatilizing a liquid within an aerosol delivery device. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

The invention claimed is:

1. An aerosol forming component for volatilizing a liquid in an aerosol delivery device, comprising:
a first aerosol-forming member controlled to be heated up to a first operating temperature and thereafter to a second higher operating temperature; and
a second aerosol-forming member controlled separated from the first aerosol-forming member to be heated up to reach the first operating temperature substantially at the same time as the first aerosol-forming member reaches the second higher operating temperature so that liquid volatilized from the first aerosol-forming member mixes with liquid volatilized from the second aerosol-forming member, wherein the first aerosol-forming member is located upstream of the second aerosol-forming member with respect to a flow of air through the aerosol delivery device in use, wherein the first and second aerosol-forming members each comprise a heater element and a wick, and wherein the heater element and the wick of each of the first and second aerosol-forming members are arranged in a common surface; further comprising: a housing comprising an air inlet and an air outlet; an aerosol chamber in fluid communication with the air inlet and the air outlet; a power source to which the first and second aerosol forming members are electrically connected; and a controller for controlling activation of the first and second aerosol-forming members.

2. The aerosol forming component according to claim 1, wherein the first and second aerosol-forming members are configured to have different heating rates, such that by activating the first and second aerosol-forming members simultaneously, the first aerosol forming member reaches the second operating temperature substantially at the same time as the second aerosol-forming member reaches the first operating temperature.

3. The aerosol forming component according to claim 1, wherein the first aerosol-forming member is activated prior to activation of the second aerosol-forming member such that the first aerosol forming member reaches the second operating temperature substantially at the same time as the second aerosol-forming member reaches the first operating temperature.

4. The aerosol forming component according to claim 1, further comprising a liquid for volatilization, wherein the liquid comprises one or more substances which create or promote an aerosol upon reaching volatilization temperature.

5. The aerosol forming component according to claim 1, wherein the liquid comprises nicotine.

6. The aerosol forming component according to claim 4, wherein the liquid comprises one or more volatile acids.

7. The aerosol forming component according to claim 4, wherein the aerosol generating means are volatilized from the first aerosol-forming member as the first aerosol-forming member reaches the second operating temperature and the one or more low boiling point fraction(s) are volatilized from the second aerosol-forming member when the second aerosol-forming member reaches the first operating temperature such that the one or more low boiling point fraction(s) settles on the aerosol generating means.

8. An aerosol delivery device comprising an aerosol forming component according to claim 1.

* * * * *